(12) United States Patent
Castro et al.

(10) Patent No.: US 6,306,407 B1
(45) Date of Patent: *Oct. 23, 2001

(54) TOPICAL MOISTURE REGULATING COMPOSITIONS

(75) Inventors: John R. Castro, Huntington Station; Michell M. Chen, Setauket; Shahan Nazar, Garden City; Janet Pardo, Brooklyn, all of NY (US)

(73) Assignee: Color Access, Inc., Melville, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/127,711

(22) Filed: Jul. 30, 1998

(51) Int. Cl.$^7$ .......................... A61K 7/027; A61K 7/025; A61K 31/74; A61K 7/00
(52) U.S. Cl. .............................. 424/401; 424/63; 424/64; 424/78.03
(58) Field of Search ............................... 424/401, 64, 63, 424/78.03

(56) References Cited

U.S. PATENT DOCUMENTS

| | | |
|---|---|---|
| 4,820,510 * | 4/1989 | Arraudeau et al. . |
| 5,182,815 | 2/1993 | Young et al. . |
| 5,234,682 | 8/1993 | Macchio et al. . |
| 5,266,321 | 11/1993 | Shukazaki et al. . |
| 5,344,698 | 9/1994 | Rock et al. . |
| 5,392,467 * | 2/1995 | Moretz et al. . |
| 5,449,341 * | 9/1995 | Harris . |
| 5,498,407 | 3/1996 | Atlas . |
| 5,533,212 | 7/1996 | Moretz et al. . |

FOREIGN PATENT DOCUMENTS

| | | |
|---|---|---|
| 03 153613 | 7/1991 | (JP) . |
| 7-179323 | 7/1995 | (JP) . |
| 07 267827 | 10/1995 | (JP) . |
| 07 267828 | 10/1995 | (JP) . |

\* cited by examiner

Primary Examiner—Thurman K. Page
Assistant Examiner—Amy Pulliam
(74) Attorney, Agent, or Firm—Kenyon & Kenyon

(57) ABSTRACT

The present invention to a cosmetic or pharmaceutical composition for topical application to the skin which comprises a fibrous component for promoting the transfer of moisture and oil and the removal of unpleasant and unwanted moisture from the skin, especially the facial skin. The fibrous component can include wicking fibers, evaporating fibers, or a combination of both. The composition of the present invention regulate moisture and oil when applied to the skin.

18 Claims, No Drawings

TOPICAL MOISTURE REGULATING COMPOSITIONS

FIELD OF THE INVENTION

The invention relates to cosmetic or pharmaceutical compositions. More specifically, the invention relates to such compositions having a fibrous component capable of transporting oil and moisture from the skin into the thin layer of the composition where evaporation of moisture is promoted.

BACKGROUND OF THE INVENTION

Cosmetics and skin care products that control oil and moisture are desirable. During the course of daily activities, especially for example, sports, physical exercise, heat or humidity, the facial skin is prone to the production of sebum and perspiration which can have negative consequences on the skin. The production of sebum leaves the skin looking oily and feeling greasy. The pores of the facial skin can become clogged by moisture and oil, and lead to acne, ugly blackheads, and other skin problems. The buildup of moisture, oil and perspiration on the facial skin simply feels uncomfortable. Makeup typically cannot endure and retain its fresh appearance when subjected to these conditions. Therefore, the skin appears less attractive. Developing cosmetics and skin care products that control unwanted moisture and oil on the facial skin is a challenge.

Cosmetic products designed to withstand the build up of moisture and oily residue tend to be heavy and drag on the skin when applied. Overall, they feel less than desirable on the skin. To achieve a product for topical application on the skin that is light, refreshing and natural feeling but, that also continues to feel as it did when it was initially applied by managing the moisture and oil on the skin, the product must be formulated to look good on the skin and perform its desired function.

In general, the use of fibers in fabrics is known for combating moisture produced on the skin. For example, in recent years, fabrics have been introduced which are capable of transporting moisture from the skin to the layer of fabric where moisture evaporates and is thereby removed from the skin. These fabrics are usually used in sports clothing. Athletes and others who are involved in physical activities typically feel uncomfortable when moisture due to perspiration builds on the surface of the skin. Clothing made with fabric that can wick away and allow for the evaporation of moisture helps them feel more comfortable. Articles of clothing utilizing this type of fabric are disclosed in U.S. Pat. Nos. 5,182,815, 5,344,698, 5,449,341, 5,533,212, 5,392,467 incorporated herein by reference. The fabric typically has at least two layers, where one layer contains hydrophilic fibers and the other layer contains hydrophobic fibers.

The hydrophobic layer initiates the transportation of moisture from the skin to the fabric and can be assisted by the hydrophilic layer. The hydrophilic layer holds moisture and is capable of allowing air to pass through, due for example, to a meshlike pattern. The passage of air through the hydrophilic layer promotes the evaporation of moisture. Once evaporated, the moisture is removed from the skin. While these fabrics are useful in removing moisture from the skin, they are limited in use because moisture is only removed from an area of the skin that is covered by the garment, and thus, clearly cannot be employed in the facial area. There thus remains a need to manage moisture on the skin, especially the facial skin, without the need to wear or have clothing in close proximity with or against the skin. The present invention achieves these goals and meets the need for the control of moisture, oil and perspiration on facial skin in a manner that is consistent with the normal daily use of foundation or other similar skin care products.

SUMMARY OF THE INVENTION

The present invention relates to a cosmetic or pharmaceutical composition for topical application to the skin which comprises a fibrous component for promoting the displacement of unpleasant and unwanted moisture and oil from the surface of the skin. The fibrous component comprises wicking fibers which wick moisture and oil outwardly away from the skin. In addition, the fibrous component can also comprise evaporating fibers that allow moisture to be evaporated off the skin. The fibrous component can therefore, be either wicking fibers, evaporating fibers, or it can contain both types of fibers. If both types of fibers are used, the fibrous component performs two basic functions and leaves the skin feeling even fresher and more comfortable. First, it draws moisture and oil away from the surface of the skin and second, it allows moisture to evaporate off of the skin. In other words, moisture and oil are oriented away from the skin and air can then vaporize the moisture absorbed by the fibers.

The present invention also includes a method of wicking moisture and oil and evaporating moisture off of the skin by applying to the skin the compositions of the present invention. The compositions keep the skin dry and comfortable even during physical activities such as strenuous exercise or during hot and humid weather. The compositions feel smooth, light and natural on the skin and do not strip the skin of essential moisture beneath the surface of the skin necessary to keep the skin healthy.

DETAILED DESCRIPTION OF THE INVENTION

The present invention is a cosmetic or pharmaceutical composition for topical application to the skin comprising a fibrous component which can contain wicking fibers, evaporating fibers or a combination of both. The fibers wick moisture and oil or evaporate moisture based on their hydrophobic and/or hydrophilic nature. The use of certain fibers in articles of clothing to control moisture is known. It is also known to include fibers in cosmetic compositions in U.S. Pat. No. 4,820,510 and JP 7179323. However, a cosmetic containing fibers to provide moisture and oil control on the skin similar to the benefit of placing clothing adjacent to the skin has not been previously suggested. In addition, the resulting cosmetic and pharmaceutical compositions of the present invention manage unwanted oil on the skin and manage moisture and eliminate the need to cover the skin with clothing in order to achieve a similar result.

Generally, in one embodiment of the present invention, the fibrous component contains wicking fibers to facilitate the transfer of moisture and oil from the surface of the skin to the composition. The composition, when applied to the skin provides a layer of fibers having moisture and oil regulating properties. On the skin, the wicking fibers create a barrier between the skin and the external environment so that oil and moisture do not break through and detract from the fresh and natural-looking appearance of the skin. In addition, the compositions maintain the natural and fresh appearance of the skin even during physical activities, exercise and other hot and humid environmental conditions.

The wicking fibers are preferably hydrophobic in order to promote the movement of oil away from the skin. Moisture is also removed from the surface of the skin by the wicking fibers. The movement of moisture by means of the wicking fibers is brought about not by the hydrophobicity of the fibers, but rather, the ability of these fibers to absorb water from the skin. The shape of the fibers supports a capillary action which allows the fibers to absorb moisture and oil. Therefore, the wicking fibers have a type of dual affinity which permits the movement of oil and moisture away from the skin.

While certain fibers are inherently hydrophobic, the fibers can also be treated to be substantially hydrophobic. Fibers treated to be hydrophobic are usually treated chemically. The term "substantially hydrophobic" means the fiber is lipophilic, oil-attracting and has a greater affinity for non-polar substances such as sebum, fatty acids, esters and other oils found on the skin than it does for other polar substances such as water.

The wicking fibers can be selected from the group consisting of nylon, polyester, polypropylene materials, and blends thereof. Other hydrophobic fibers, such as polyester may be used as, for example fibers under the tradenames COOLMAX™ and THERMAX™ which are manufactured by DuPont of Wilmington, Del.

In a more preferred embodiment of the present invention, the fibrous component comprises wicking fibers that can be in the form of nylon fibers. Nylon is inherently hydrophobic, however, it also absorbs water by the capillary type of action and has a dual affinity. The nylon has a denier (dpf) from about 0.8 to about 20. The length of the nylon fiber is from about 0.01 to about 0.25 inches. The moisture regain of the nylon fiber is from about 4.0 to about 4.5 percent at about 70° F. and about 65 percent relative humidity. Preferably, the nylon fibers are microdenier fibers of nylon-6.

In another embodiment of the present invention, the compositions contain evaporating fibers which allow moisture to evaporate off of the surface of the skin. Preferably, these fibers are hydrophilic or they can be treated to be substantially hydrophilic. The term "substantially hydrophilic" means that the fiber is attracted to water and has a greater affinity for water than it does for oil. The evaporating fibers can be selected from the group consisting of polyethylene, polypropylene, acrylic, aramid, rayon, cotton, wool, silk and blends thereof. An example of treated hydrophilic nylon fibers are Intera-treated nylon fibers processed by the Intera Corporation of Cleveland, Tenn., and nylon-6 copolymer under the tradename HYDROFIL™ manufactured by Allied Signal Fibers of Petersburg, Va. Other similarly treated fabrics such as a modified polyester under the tradename THERMASTAT™, manufactured by DuPont of Wilmington, Del., and a modified acrylic under the tradename DUNOVA™, manufactured by Bayer of Leverkusen of Germany are available. Other manufacturers of fabrics can be used as well.

In yet another embodiment of the present invention, the cosmetic or pharmaceutical composition comprises evaporating fibers and wicking fibers (i.e., the two fibers are present in the composition together). The combination of these two fibers randomly dispersed in the composition work synergistically together to provide combined benefits. Moisture and oil are lifted off of the skin by the presence of the wicking fibers, but in addition to that, the evaporating fibers promote the evaporation of moisture that has been lifted away from the surface of the skin by the wicking fibers. Air passes through the evaporating fibers and permits evaporation of moisture because the fibers are oriented in a natural manner that allows air to pass through. The skin feels more comfortable when moisture is no longer settled on the surface of the skin.

The fibrous component is present in an amount sufficient to provide moisture and oil regulation without appearing fuzzy on the surface of the skin when applied. A sufficient amount of fiber also gives the composition a natural look on the skin similar to that of the natural ultrafine hairs that exist on the surface of the skin. In a preferred embodiment of the present invention, the fibrous component is present in an amount of from about 0.005 to about 1.0 percent by weight, preferably it is present in an amount of from about 0.01 to about 0.5 percent by weight. The shape of the fibers can be any assortment of shapes such as round, bean, bone, oval, trilobal, irregular, or other fiber like shapes. Preferably the fibers are round. Moisture regain of the fibers is generally from about 0.001 to about 1.0 percent at about 70° F. and about 65 percent relative humidity. Higher temperatures and lower levels of humidity may enhance the performance of the composition. The fiber can be in the form of flock having a length from about 0.01 to about 0.25 inches.

The composition also includes a compatible carrier. By "compatible carrier" in the present specification and claims is meant any cosmetically acceptable carrier which is compatible with the fibers. The carrier may contain one or more oil components. The oil component may be any pharmaceutically or cosmetically acceptable material which is substantially insoluble in water. These materials can be found for example in the CTFA International Dictionary of Cosmetic Ingredients as well as the U.S. Pharmacopoeia or other equivalent sources. Suitable oil components include, but are not limited to, natural oils, such as coconut oil; hydrocarbons, such as mineral oil and hydrogenated polyisobutene; fatty alcohols, such as octyldodecanol; esters, such as C12–15 alkyl benzoate; diesters, such as propylene glycol dipelargonate; triesters, such as glyceryl trioctanoate; sterol derivatives, such as lanolin; animal waxes, such as beeswax; plant waxes, such as carnauba; mineral waxes, such as ozokerite; petroleum waxes, such as paraffin wax; synthetic waxes, such as polyethylene; and mixtures thereof.

Suitable oil components may also be silicones. The silicone oil can be volatile or semi-volatile, or any combination thereof. Suitable volatile oils include cyclic and linear silicones, such as hexamethylcyclotrisiloxane, octamethylcyclotetrasiloxane, and decamethylcyclopentasiloxane or volatile linear dimethylpolysiloxanes; or mixtures thereof. Other volatile silicones include, but are not limited to, cyclomethicone; polymeric silicones such as dimethicone; alkylated derivatives of polymeric silicones, such as cetyl dimethicone and lauryl trimethicone; hydroxylated derivatives of polymeric silicones, such as dimethiconol; and mixtures thereof. The carrier comprises, in the composition as a whole, preferably silicone oil which is present in an amount of at least about 0.5 to about 60 percent by weight. Preferably, the compatible carrier is one that enhances the soft powdery feel of the composition. A particularly preferred carrier is a low volatile silicone oil.

The ability of the composition to breathe is enhanced by the use of the low volatile silicone carrier which is permeable in general, and allows water vapor to pass through the composition. Further, the inclusion of a permeable film forming agent also enhances the breathability of the compositions. Accordingly, the composition of the present invention includes one or more film-forming agents. The use of a film-former can also improve the wear of the composition, and can confer transfer-resistance to the makeup product. Examples of useful film-forming agents include natural waxes, polymers such as polyethylene polymers and copolymers of PVP, dimethicone gum, and resins, such as shellac, polyterpenes, and various silicone resins. A particularly preferred film-former is trimethylsiloxysilicate, used in an amount of from about 0.1 to about 20 percent by weight of the total composition.

The composition of the present invention can also include polyurethane and derivatives thereof as, for example, trimethylol crosslinked polyurethane. While the compositions have a soft powdery feel due to the fiber content, the presence of polyurethane also contributes to the dry and powdery feel. Polyurethane is a slip agent which makes it easier to apply the composition to the skin. Therefore, the composition applies smoothly to the skin without the need to add oil and yet, does not drag or cake on the skin.

The present invention also includes a method of wicking moisture and oil and evaporating moisture off of the skin comprising applying to the skin the cosmetic or pharmaceutical composition which comprises a fibrous component. The compositions are especially beneficial when used on the facial skin. However, they can be used on the skin on any area of the body where there is a need to relieve the discomfort of unwanted moisture and oil.

The benefit of adding fibers to cosmetic or pharmaceutical compositions can be obtained in any type of makeup composition, for example, foundations, eyeshadows, blushes, powders, lipsticks and lipglosses. In a preferred embodiment, the compositions of the present invention are used in a foundation. However, the benefit of the present invention can also be obtained in non-makeup compositions, (e.g., treatment products) wherein the product is applied to the skin for a therapeutic purpose, but also has the added advantage of controlling oil and moisture on the skin. Finally, the topical product may be applied solely for the purpose of oil and moisture control.

In another embodiment of the present invention, the composition is a lipstick comprising a fibrous component in which case, it may also be desirable to incorporate one or more waxes in the composition. The term "wax" will be understood to encompass not only waxes in the traditional sense, i.e., those plant, animal or mineral waxes containing primarily esters of higher fatty acids and alcohols, free higher acids and alcohols, and saturated hydrocarbons, but also synthetic resinous products having a wax-like, i.e., hard, brittle, relatively non-greasy texture at room temperature, such as silicone waxes. Examples of suitable waxes include, but are not limited to, carnauba wax, candelilla wax, beeswax, microcrystalline wax, polyethylene, japan wax, synthetic wax, shellac wax, spermaceti, lanolin wax, ozokerite, bran wax, ceresin wax, bayberry wax, paraffin, rice wax, mink wax, montan wax, ouricoury wax, jojoba wax, and the like.

Additional preferred components of the cosmetic compositions of the invention include one or more pigments. Any cosmetically acceptable pigment, either organic, inorganic, or combinations thereof, can be used in the makeup compositions of the invention. Examples of useful inorganic pigments include iron oxides (yellow, red, brown or black), ultramarines, chromium hydroxide green, chromium oxide, titanium dioxide (white), ferric ferrocyanide, ferric ammonium ferrocyanide, and mixtures thereof.

The organic pigments include natural colorants and synthetic monomeric and polymeric colorants. Exemplary are aromatic compounds such as azo, triphenylmethane, indigo. anthraquinone, and xanthine dyes, which are referred to as D&C or FD&C pigments. Also useful are lakes, which are pigments formed by the precipitation and absorption of organic dyes on an insoluble base, such as alumina, barium, or calcium hydrates. Particularly preferred lakes are primary FD&C or D&C lakes and blends thereof. In a preferred embodiment the pigment employed is hydrophobically treated. Such treatment assists in preventing oil breakthrough, and further aids in keeping the color true. Examples of useful hydrophobic surface treatments include but are not limited to amino acids, silicones, methicones, dimethicones, silanes, polyethylene, metal soaps, lecithin, waxes, nylon, or flourochemicals. Pigment concentrations will vary depending upon the color of the final product, but generally will be in the range of from about 5.0 to about 20 percent by weight of the total composition. Further, the fibers themselves can be pigmented.

The composition can also contain small amounts of fillers or powders. Examples of such include silica, talc, mica, starch, nylon, kaolin, bismuth oxychloride, or coated versions of each of these, for example, with lecithin, silicones, amino acids, fatty acids, fatty alcohols, or metallic soap coatings. The addition of fillers or powders enhance the dry and powdery feel.

Another optional component of the composition is a metal stearate, where the metal is selected from the group consisting of zinc, calcium, copper, aluminum, lithium and magnesium. The presence of a metal stearate assists in the transfer resistance of the composition, and also improves the feel of the composition.

The composition can also contain other optional components including, but not limited to, oil soluble sunscreens, such as octyl methoxycinnamate; particulate sunscreens such as zinc oxide; oil-soluble antioxidants and/or preservatives, such as BHT; chelating agents such as Disodium EDTA; fragrances (such as pinene); flavoring agents; waterproofing agents (such as PVP/eicosene copolymer); surfactants, such as silicone copolyols or fatty acid glycerol esters; and oil-soluble actives, such as tocopherol and its derivatives or retinol and its derivatives; and the like.

The invention is further illustrated by the following non-limiting example.

EXAMPLES

I. Foundation formulation

| Material | Weight % |
| --- | --- |
| Phase I | |
| Cetyl dimethicone copolyol | 0.5 |
| Cyclomethicone | 25 |
| Trioctanoin | 1 |
| Isostearyl palmitate | 1 |
| Zinc stearate | 2 |
| Nylon-12 | 6 |
| Silk powder | 0.1 |
| Pigments | 5 |
| Phase II | |
| Trimethyl siloxy silicate | 5 |
| Phase III | |
| Dimethicone copolyol | 3 |
| Phase IV | |
| Butylene glycol | 7 |
| Purified water | 41.55 |
| Sodium Chloride | 1.5 |
| Laureth-7 | 0.3 |

-continued

| I. Foundation formulation | |
|---|---|
| Material | Weight % |
| *Phase V* | |
| Nylon-6 | 0.05 |
| Preservatives | 1 |

The Phase I constituents of the above formula are mixed together using a high speed propeller mixer. After mixing, the Phase I constituents are ground using appropriate equipment until no streaking is apparent. In a separate kettle, Phase I and Phase II constituents are combined and mixed together. In another vessel, Phase III constituents are combined using a high speed propeller mixer. When Phase III constituents are clear, it is slowly added to the Phase I and Phase II batch. To this mixture, the Phase IV constituents are added and mixed. Phase V constituents are slowly swept into the batch and mixed.

II. Measurement of Moisture and Oil Regulation

A makeup foundation containing fibers, according to the present invention, is tested using a panel of 30 female individuals. Qualifying panelists are selected from ages 18 to 55. They have normal, normal-oily, or oily facial skin, engage in outdoor activity or exercise at least 3 days per week, and are regular users of a liquid, transfer-resistant foundation at least 5 days a week. Chosen panelists participate in an unidentified one day monadic study and complete a questionnaire at the close of the study. The questionnaire allows the panelists to rate various properties of the composition of the present invention. The panelists respond to questions about the properties of the composition using a five point scale (e.g. ranging from excellent to poor).

Various portions of the questionnaire correspond to different characteristics of the composition. For example, a Performance Rating portion of the questionnaire examines the ability of the composition to maintain its appearance on the skin throughout the day, the texture of the composition whether the composition feels greasy or oily on the skin, whether the composition is transfer-resistant, and whether the composition helps control moisture or perspiration breakthrough (i.e. whether the composition regulates moisture). The scale for this portion ranges from excellent to poor. Another portion of the questionnaire, entitled "Appearance of Skin During Day", examines in more detail how the composition appears on the skin throughout the period of a day. This portion is divided into a five point rating scale having categories of "like a lot", "like somewhat", "neither like nor dislike", "dislike somewhat", to "dislike a lot".

The questionnaire also has a portion entitled "Comfort of Skin While Wearing the Test Foundation During Outdoor Activity or Exercise", which probes the level of comfort the panelist feels while exercising with the composition worn on the skin. The five point scale for this rating is "very comfortable", "somewhat comfortable", "neither comfortable nor uncomfortable", "somewhat uncomfortable", to "very uncomfortable". Finally, a portion of the questionnaire entitled "Effectiveness at Controlling Oil, Moisture, and Perspiration Breakthrough While Wearing the Test Foundation During Outdoor Activity or Exercise", looks at the ability of the composition to effectively manage oil, moisture and perspiration. It is divided into categories of "extremely effective", "very effective", "somewhat effective", "only a little effective", "not at all effective".

The results of the questionnaire for the Performance Rating indicate that a rating of excellent/very good is made by 24 out of 30 panelists for the appearance of skin after application, by 23 out of 30 panelists for being long wearing, and by 22 out 30 panelists for maintaining its appearance throughout the day and for feeling natural on the skin. With respect to oil and moisture management, 20 out of 30 find the composition is excellent/very good at helping to control oil breakthrough, 19 out of 30 find the composition is excellent/very good at allowing the skin to breathe while wearing makeup, and 17 out of 30 find the composition is excellent/very good at helping to control moisture or perspiration breakthrough. In the Appearance of Skin During Day portion of the questionnaire, 28 out of 30 panelists find that they like the composition a lot or like the composition somewhat.

With respect to the section for the Comfort of Skin While Wearing the Test Foundation During Outdoor Activity or Exercise, 15 out of the 30 panelists engage in outdoor activity or exercise while wearing the composition. Out of those 15 panelists, 14 find the composition to be very or somewhat comfortable; and 11 out of 15 panelists rate the composition extremely/very effective at controlling oil, moisture, and perspiration breakthrough. In addition, the portion rating the Effectiveness at Controlling Oil, Moisture, and Perspiration Breakthrough While Wearing the Test Foundation During Outdoor Activity or Exercise reveals that the composition, according to 11 out of 15 panelists, is extremely or very effective. Finally, 14 out of 15 of the panelists find the composition maintains its appearance during exercise.

What we claim is:

1. A cosmetic or pharmaceutical composition for topical application to the skin, said composition comprising a fibrous component which comprises nylon microdenier wicking fibers having a length from about 0.01 to about 0.25 inches and treated to render them hydrophobic in combination with a cosmetically compatible carrier.

2. The composition of claim 1 in which said hydrophobic fibers are further selected from the group consisting of polyester, polypropylene, and blends thereof.

3. The composition of claim 2 wherein said fibers are nylon-6.

4. A cosmetic or pharmaceutical composition for topical application to the skin, said composition comprising a fibrous component which comprises substantially hydrophilic nylon microdenier evaporating fibers having a length from about 0.01 to about 0.25 inches and treated to render them hydrophilic in combination with a cosmetically compatible carrier.

5. The composition of claim 4 in which said substantially hydrophilic fibers are selected from the group consisting of polyethylene, polypropylene, acrylic, aramid, rayon, cotton, wool, silk and blends thereof.

6. The composition of claim 5 wherein said fibers are nylon-6.

7. The composition of claim 1 which further comprises one or more pigments.

8. The composition of claim 1 which is a lipstick.

9. The composition of claim 1 which is a foundation.

10. A cosmetic or pharmaceutical composition for topical application to the skin comprising a fibrous component which comprises substantially hydrophobic nylon microdenier wicking fibers treated to be hydrophobic and substantially hydrophilic nylon microdenier evaporating fibers treated to be hydrophilic having a length from about 0.01 to about 0.25 inches in combination with a cosmetically compatible carrier.

11. The composition of claim 10 wherein said fibers are present from about 0.005 to about 1.0 percent by weight.

12. The composition of claim 10 which comprises one or more pigments in an amount of from about 0.1 to about 30 percent by weight.

13. The composition of claim 10 which comprises a film forming agent in an amount of from about 0.1 to about 20 percent by weight.

14. The composition of claim 13 in which the film forming agent is trimethylsiloxysilicate.

15. The composition of claim 11 which comprises polyurethane.

16. The composition of claim 11 which comprises metal stearate.

17. The composition of claim 11 which is a lipstick or a foundation.

18. A method of wicking oil and moisture and evaporating moisture comprising applying to the skin the composition of claim 1.

* * * * *